(12) United States Patent
Halden (10) Patent No.: US 7,662,618 B2
(45) Date of Patent: Feb. 16, 2010

(54) METHOD AND APPARATUS FOR ENVIRONMENTAL MONITORING AND BIOPROSPECTING

(75) Inventor: Rolf U. Halden, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 213 days.

(21) Appl. No.: 10/797,713

(22) Filed: Mar. 10, 2004

(65) Prior Publication Data
US 2004/0180334 A1 Sep. 16, 2004

Related U.S. Application Data

(60) Provisional application No. 60/453,411, filed on Mar. 10, 2003, provisional application No. 60/463,394, filed on Apr. 16, 2003, provisional application No. 60/485,475, filed on Jul. 8, 2003, provisional application No. 60/528,256, filed on Dec. 9, 2003, provisional application No. 60/541,781, filed on Feb. 4, 2004.

(51) Int. Cl.
*C12M 1/32* (2006.01)

(52) U.S. Cl. ............... 435/309.1; 435/288.4; 435/287.2; 73/863.23; 73/863.31; 73/863.71; 73/864.63; 73/864.67; 166/107; 166/165; 166/167; 166/246

(58) Field of Classification Search .............. 435/288.4, 435/297.2, 309.1; 73/864.33, 864.64, 864.67; 73/863.23, 863.31, 863.71; 166/107, 165, 166/167, 264
See application file for complete search history.

(56) References Cited

U.S. PATENT DOCUMENTS 2,609,878 A * 9/1952 Halliburton ................. 166/107

(Continued)

OTHER PUBLICATIONS

Halden, R. U., B. G. Halden, and D. F. Dwyer, "Removal of dibenzofuran, dibenzo-p-dioxin, and 2-chlorodibenzo-p-dioxin from soils inoculated with *Sphingomonas* sp. strain RW1." *Appl. Environ. Microbiol.*, 65:2246-2249 (1999).

(Continued)

*Primary Examiner*—William H Beisner
(74) *Attorney, Agent, or Firm*—Edwards Angell Palmer & Dodge LLP; Peter F. Corless (57) ABSTRACT

A method for environmental monitoring and bioprospecting includes the steps of: (a) utilizing a testing device having: (i) a container having a fluid inlet and outlet, (ii) a plurality of capillary microcosms situated within the container, each of these capillaries having an inlet and outlet that are configured so as to allow for fluid flow through the capillaries, each of these capillaries further having a means for covering its inlet and outlet so as to prevent flow through the capillary, (iii) a pump connected to the container outlet, the pump being configured so as to draw fluid from the surrounding environment into the container's inlet and through the capillaries, (iv) connected to the outlet of the container, a means for collecting the flow through the container, and (v) a check valve connected downstream of the container to prevent the backflow of fluid into the container, (b) adding specified test substances to the device's capillaries, wherein these substances are to be analyzed for their ability to accelerate a specified biotransformation process in the subject environment, (c) locating this device in this environment and opening the capillary covering means so as to allow fluid from the surrounding environment to flow though the container and capillaries, (d) leaving the device in situ for a temporal duration sufficient to incubate phenomena occurring within the capillary microcosms, (e) retrieving the testing device, and (f) analyzing phenomena occurring with the capillary microcosms using automated analysis schemes and commercially available robotics.

22 Claims, 4 Drawing Sheets

U.S. PATENT DOCUMENTS

| | | | | |
|---|---|---|---|---|
| 5,138,890 | A | 8/1992 | Wood | 73/864 |
| 5,349,874 | A | 9/1994 | Schapira et al. | 73/864 |
| 5,369,011 | A | 11/1994 | Ebersole | 435/7.32 |
| 5,559,295 | A | 9/1996 | Sheryll | 73/864 |
| 5,686,299 | A | 11/1997 | Colwell et al. | 435/287 |
| 6,004,766 | A | 12/1999 | Atrache et al. | 435/7.94 |
| 6,174,673 | B1 | 1/2001 | Short et al. | 435/6 |
| 6,365,368 | B1 | 4/2002 | Minnich et al. | 435/34 |
| 6,561,046 | B1 | 5/2003 | Taylor et al. | 73/863 |
| 2005/0074834 | A1 | 4/2005 | Chaplen et al. | |

OTHER PUBLICATIONS

Halden, R. U., E. G. Peters, B. G. Halden, and D. F. Dwyer, "Transformation of mono- and dichlorinated phenoxybenzoates by phenoxybenzoate-dioxygenase in *Pseudomonas pseudoalcaligenes* POB310 and a modified diarylether-metabolizing bacterium," *Biotechnol. Bioeng.* 69:107-112 (2000).

Halden, R. U., S. M. Tepp, B. G. Halden, and D. F. Dwyer, "Degradation of 3-phenoxybenzoic acid in soil by *Pseudomonas pseudoalcaligenes* POB310 (pPOB)," *Appl. Environ. Microbiol.* 65:3354-3359 (1999).

Lowe, M., E. L. Madsen, K. Schindler, C. Smith, S. Emrich, F. Robb, and R. U. Halden, "Geochemistry and microbial diversity of a trichloroethene-contaminated Superfund site undergoing intrinsic in situ reductive dechlorination," *FEMS Microbiology Ecology* 40:123-134 (2002).

Vancheeswaran, S., R. U. Halden, K. J. Williamson, J. D. Ingle, and L. Semprini, "Abiotic and biological transformation of tetraalkoxysilanes and trichloroethene/cis-1,2-dichloroethene cometabolism driven by tetrabutoxysilane-degrading microorganisms," *Environ. Sci. Technol.* 33:1077-1085 (1999).

Vancheeswaran, S., S. H. Yu, P. Daley, R. U. Halden, K. J. Williamson, J. D. Ingle, and L. Semprini, "Intrinsic remediation of trichloroethene driven by tetraalkoxysilanes as co-contaminants: results from microcosm and field studies," *Remediation* 13/14:7-25 (2003).

* cited by examiner

|   | A | B | C | D | E | F | G | H | I | J | K | L |
|---|---|---|---|---|---|---|---|---|---|---|---|---|
| i |   | a | b | c | d | e | f | g | h | a5 | a10 | a50 |
| ii | [m] | [n] | m | n | o | p | q | r | s | p<br>S | [p]<br>[S] |   |
| iii | S | T |   |   |   |   |   |   |   |   |   |   |
| iv |   | a | b | c | d | e | f | g | h | a5 | a10 | a50 |
| v | [m] | [n] | m | n | o | p | q | r | s | p<br>S | [p]<br>[S] |   |
| vi |   | a | b | c | d | e | f | g | h | a5 | a10 | a50 |
| vii | [m] | [n] | m | n | o | p | q | r | s | p<br>S | [p]<br>[S] |   |
| viii |   | a | b | c | d | e | f | g | h | a5 | a10 | a50 |

METHOD AND APPARATUS FOR ENVIRONMENTAL MONITORING AND BIOPROSPECTING

CROSS-REFERENCE TO RELATED APPLICATION

This application claims the benefit of the following U.S. Provisional Patent Applications: Nos. 60/453,411, filed Mar. 10, 2003; 60/463,394, filed Apr. 16, 2003; 60/485,475, filed Jul. 8, 2003; 60/528,256, filed Dec. 9, 2003 and 60/541,781, filed Feb. 4, 2004; all these applications having been filed by Rolf U. Halden and assigned to The Johns Hopkins University.

BACKGROUND OF THE INVENTION

1. Field of the Invention

This invention relates to measuring and testing of environmental and biological phenomena. More particularly, the present invention relates to methods and apparatuses for environmental monitoring and bioprospecting.

2. Description of Prior Art

Bioremediation is an effective, yet inexpensive biotechnology for removing organic and inorganic pollutants from contaminated environments. When targeting dissolved metals and radionuclides, the goal is to convert water-soluble, toxic species to insoluble, less toxic products. For example, uranium may be removed from contaminated groundwater and immobilized in the subsurface via the injection of carbon sources that stimulate the microbially induced precipitation of dissolved U(VI) in the form of insoluble U(IV). In this case, the contaminant is being treated "in place" and the process is being referred to as in situ bioremediation.

When designing in situ bioremediation strategies, it is essential to gain an understanding of the type, activity, and nutritional requirements of subsurface microbial communities present at a specific cleanup site. Microbial community information also is important for convincing regulatory agencies and stakeholders that the contaminant is being removed (or, in the case of metals, successfully immobilized in the subsurface) rather than being diluted or dispersed in groundwater.

Currently, the assessment of bioremediation potential at a given site is both labor- and cost-intensive. A typical approach for implementing bioremediation includes the following two steps: (1) Microcosm screening studies conducted in the laboratory to determine the extent of intrinsic bioremediation and to identify the type, quantity and frequency of carbon source injection that may be needed in order to accelerate the in situ bioremediation process; these experiments also serve to estimate contaminant removal rates but do not accurately reflect actual in situ removal rates due to the biases introduced by laboratory "bottle effects," and (2) Microbial community profiles are obtained from microcosm and field samples to determine the microorganisms responsible for the desired biotransformation reactions; since most microorganisms fail to grow on laboratory media, culture-independent profiling techniques are commonly used, (e.g., 16S rDNA-based analyses).

Groundwater is the usual preferred sample matrix for profiling of microbial communities, as it is both readily available and inexpensive. Unfortunately, the lifestyle of a given target organism has a significant impact on one's ability to detect it in this matrix. In the extreme, a target organism pursuing a sessile lifestyle throughout its existence will be impossible to detect in groundwater at a site even if it is present at extremely high densities. Thus, groundwater monitoring alone may not accurately reflect the microbial community composition and dynamics of subsurface environments. Recently, solid-phase samplers were rediscovered as useful tools for overcoming some of these limitations.

In their simplest configuration, solid-phase samplers are nothing more than a physical surface incubated in an environment of interest for a period of time sufficiently long to allow for the colonization by microorganisms. Buried or submerged glass slides have been used extensively to collect microorganisms from soils, bioreactors and other environments. Following retrieval of such samplers, microorganisms are extracted and identified via the detection of biomarkers including DNA, phospholipids, fatty acids and respiratory quinones. An argument can be made that microorganisms collected with a solid-phase sampler are more representative of the metabolically active microbial community than those obtained by groundwater sampling because the sampling device requires the active physical attachment by the microorganisms to be captured. However, dead microorganisms, cell debris and DNA also may become entrapped. Highly sensitive tools (e.g., the polymerase chain reaction, PCR) can detect biomarkers in non-living material as well as those of metabolically active microbial community members.

Recently, stable-isotope markers have been used to distinguish metabolically active microorganisms from those being dormant or non-viable. Stable isotope probing (SIP) exploits the fact that the DNA of an organism growing on carbon-13 enriched carbon sources becomes $^{13}C$-labeled ("heavier"), thereby enabling one to resolve its DNA from the total community DNA by density gradient centrifugation. While representing a powerful research tool, stable isotope probing appears to have limited potential for being applied for routine biological monitoring since the technique is very time- and labor-intensive.

An alternative approach for the identification of microorganisms is to look for gene expression products (i.e., proteins) rather than for their characteristic DNA sequences. This can be done with the latest generation of mass-spectrometry instrumentation that offers sufficient speed and sensitivity, while also allowing for complete automation of the analysis process.

Matrix assisted laser desorption ionization (MALDI) time-of-flight (TOF) mass spectrometry (MS), with its ability to induce desorption of protein biomarkers from intact bacteria, fungi, spores and viruses, provides a powerful and rapidly emerging technology for fast, portable and robust microorganism identification. MALDI-TOF-MS techniques are very rapid (<5 minutes analysis time per sample), have low sample volume requirements (<1 mL) and have a generic capability to identify microorganisms.

Robotic devices recently have been integrated with MALDI-TOF instruments to provide for automation of this analysis technique. The latest generation of commercially available robotics allows for the fully automated sample preparation and analysis, including preparation and imaging of 2D gels, harvesting and digestion of the protein spots, and application of the digests to multi-sample MALDI-TOF targets for analysis.

Despite all the prior art in this field, there still exists an ongoing need for improved testing methods and apparatus. For example, a methodology and technology that could integrate the above technologies so as to provide for both microbial community profiles and microcosm screening studies in a one-step, lower cost process would contribute greatly to this field. Ideally, such a fully developed methodology and technology would yield information on what types of organisms are present, which are alive and metabolically active, what type of nutrients and nutrient dosages should be used to accelerate bioremediation, and what in situ bioremediation rates would result.

Such a new methodology and technology should also prove to be quite valuable in other in situ applications; for example, in bioprospecting in saturated media, i.e., for the discovery of novel microorganisms, biochemical reactions, and natural products. Since less than an estimated one percent of environmental microorganisms are thought to be capable of growing and functioning under laboratory conditions, a new methodology and tool for exploring in situ microbial processes could effectively open the research door to a large fraction of the uncharted microbial world.

The underlying rationale of such an invention would be—since the majority of microorganisms do not tolerate the transfer from their natural habitat to the laboratory—to deliver the laboratory to the microorganisms. The impact of such an invention would be to benefit both human and environmental health by accelerating the discovery of novel microorganisms, enzymes and metabolic processes.

The present inventor has been working in this technical field and towards the development of such an improved methodology for some time. Much of his earlier research is applicable to the methodologies described herein. Most of this work has been documented in the scientific literature. See for example: Franklin, M. P., V. Madrid, S. Gregory, and R. U. Halden, "Spatial Analysis of a Microbial Community Mediating Intrinsic Reductive Dechlorination of TCE to cis-DCE at a DOE Superfund Site," presented at the 103rd ASM General Meeting, Washington, D.C., May 18-22, 2003; Halden, R. U., B. G. Halden, and D. F. Dwyer, "Removal of dibenzofuran, dibenzo-p-dioxin, and 2-chlorodibenzo-p-dioxin from soils inoculated with *Sphingomonas* sp. strain RW1." *Appl. Environ. Microbiol.*, 65:2246-2249 (1999); Halden, R. U., E. G. Peters, B. G. Halden, and D. F. Dwyer, "Transformation of mono- and dichlorinated phenoxybenzoates by phenoxybenzoate-dioxygenase in *Pseudomonas pseudoalcaligenes* POB310 and a modified diarylether-metabolizing bacterium," *Biotechnol. Bioeng.* 69:107-112 (2000); Halden, R. U., S. M. Tepp, B. G. Halden, and D. F. Dwyer, "Degradation of 3-phenoxybenzoic acid in soil by *Pseudomonas pseudoalcaligenes* POB310(pPOB)," *Appl. Environ. Microbiol.* 65:3354-3359 (1999); Colquhoun, D., E. S. Wisniewski, D., A. Kalmykov, and R. U. Halden, "Identification of *Sphingomonas wittichii* RW1 Through the Dioxin Dioxygenase Enzyme Using Mass Spectrometry. 104th General Meeting of the American Society for Microbiology, New Orleans, La., May 23-27 (2004); Halden, R. U., R. N. Cole, C. Bradford, D. Chen, and K. J. Schwab, "Rapid Detection of Norwalk Virus-like Particles using MALDI-TOF MS and ESI-MS/MS," 51 st Meeting of the American Society for Mass Spectrometry, Montreal, Quebec, Canada, Jun. 8-12, 2003, http://www.inmerge.com/aspfolder/ASMSSchedule2.asp; Lowe, M., E. L. Madsen, K. Schindler, C. Smith, S. Emrich, F. Robb, and R. U. Halden, "Geochemistry and microbial diversity of a trichloroethene-contaminated Superfund site undergoing intrinsic in situ reductive dechlorination," *FEMS Microbiology Ecology* 40:123-134 (2002); Vancheeswaran, S., R. U. Halden, K. J. Williamson, J. D. Ingle, and L. Semprini, "Abiotic and biological transformation of tetraalkoxysilanes and trichloroethene/cis-1,2-dichloroethene cometabolism driven by tetrabutoxysilane-degrading microorganisms," *Environ. Sci. Technol.* 33:1077-1085 (1999); and Vancheeswaran, S., S. H. Yu, P. Daley, R. U. Halden, K. J. Williamson, J. D. Ingle, and L. Semprini, "Intrinsic remediation of trichloroethene driven by tetraalkoxysilanes as co-contaminants: results from microcosm and field studies," *Remediation* 13/14:7-25 (2003). The teachings and disclosure of these works are hereby incorporated herein by reference.

3. Objects and Advantages

There has been summarized above, rather broadly, the background that is related to the present invention in order that the context of the present invention may be better understood and appreciated. In this regard, it is instructive to also consider the objects and advantages of the present invention.

It is an object of the present invention to provide an improved, lower cost method for environmental monitoring and bioprospecting.

It is another object of the present invention to provide an improved bioremediation assessment method and tool that will more effectively support the environmental restoration and long-term stewardship of contaminated sites. It is yet another object of the present invention to provide an improved bioremediation assessment method and tool that will enable the automated, large-volume, high-throughput analysis of bioremediation sites.

It is a further object of the present invention to provide a monitoring method, tool and analysis strategy that allow for the automated, rapid and simultaneous determination of the following parameters: (1) fluid quality and toxicity, (2) intrinsic bioremediation potential, (3) accelerated bioremediation potential following nutrient amendment, (4) effective bioaugmentation strategies for environmental cleanup, (5) turnover rates of natural compounds and environmental pollutants under natural and enhanced conditions, (6) in situ DNA synthesis and protein expression, (7) in situ growth/death rates and metabolic activity of native and introduced biological agents under natural and altered environmental conditions, (8) structure and dynamics of microbial communities indigenous to natural environments, and (9) identity and activity of microorganisms of potential value for use in biotechnology.

It is an object of the present invention to provide a monitoring method and tool that may be applied to assess the potential risk resulting from the release of nonindigenous microorganisms, pathogens and genetically engineered microorganisms into natural environments.

It is another object of the present invention to provide a method and tool that have potential value for discovering microorganisms, enzymes and natural products of relevance for the pharmaceutical industry and the biotechnology sector.

These and other objects and advantages of the present invention will become readily apparent as the invention is better understood by reference to the accompanying summary, drawings and the detailed description that follows.

SUMMARY OF THE INVENTION

Recognizing the needs for the development of improved methods and apparatuses for environmental monitoring and bioprospecting, the present invention is generally directed to satisfying the needs set forth above and overcoming the disadvantages identified with prior art devices and methods.

In a first preferred embodiment, such a method comprises the steps of: (a) locating a sampling device in an environment to be investigated, wherein this device comprises: (i) a container having a fluid inlet and outlet, (ii) a plurality of capillary microcosms situated within the container, each of these capillaries having an inlet and outlet that are configured so as to allow for fluid flow through the capillaries, each of these capillaries further having a means for covering its inlet and outlet so as to prevent flow through the capillary, (iii) a pump connected to the container inlet, the pump being configured so as to draw fluid from the surrounding environment, following which it is forced into the container's inlet and through the capillaries, (iv) connected to the outlet of the container, a means for collecting the flow forced through the capillaries by the pump, and (v) a check valve connected downstream of the container to prevent the backflow of fluid into the container, this plurality of capillaries being configured so as to allow for automated analysis of the capillaries using commercially available robotics, (b) opening the capillary covering means so as to allow fluid from the surrounding environment to flow though the container and capillaries, (c) leaving the device in situ for a temporal duration termed incubation period sufficient to study phenomena occurring within the capillary microcosms, (d) retrieving the testing device, and (e) analyzing phenomena occurring with the capillary microcosms using real-time sensors, automated analysis schemes and commercially available robotics.

In another preferred embodiment, the present invention takes the form of the method described above plus the step of performing, with the device, a screening study between specified test substances added to the capillaries for their assumed ability to accelerate a specified bioremediation process in the subject environment.

In a still further preferred embodiment, the present invention takes the form of a testing device for environmental monitoring of and bioprospecting for microorganisms within a specified environment. This embodiment comprises: (a) a container having a fluid inlet and outlet, (b) a plurality of capillary microcosms situated within the container, each of the capillaries having a capillary inlet and outlet that are configured so as to allow for fluid flow through the capillaries, each of the capillaries further having a means for covering the capillary inlet and outlet so as to prevent flow through the capillary, (c) a pump connected to the container inlet, the pump being configured so as to draw fluid from the surrounding environment and force it through the container's inlet and the capillaries, (d) connected to the outlet of the container, a means for collecting the flow forced through the capillaries by the pump, and (e) a check valve connected downstream of the container to prevent the backflow of fluid into the container, wherein the plurality of capillaries being configured so as to allow for automated analysis of the capillaries using commercially available robotics.

In yet another preferred embodiment, the present invention takes the form of the testing device described above and wherein the plurality of capillaries are configured so as to aid in the identification of microorganisms indigenous to the environment surrounding in situ location of the container.

Thus, there has been summarized above, rather broadly, the present invention in order that the detailed description that follows may be better understood and appreciated. There are, of course, additional features of the invention that will be described hereinafter and which will form the subject matter of any eventual claims to this invention.

DETAILED DESCRIPTION OF THE PREFERRED EMBODIMENT

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As previously mentioned, the present invention can serve many purposes, including: the management and bioremediation of contaminated sites, the detection of microorganisms in terrestrial and extra-terrestrial environments, the risk assessment of microorganisms introduced into natural environments, and the search for novel microorganisms, enzymes and/or compounds applicable to biotechnology.

The present invention provides both a monitoring tool and an analysis strategy or method. These allow for the automated, rapid and simultaneous determination of many key bioremediation parameters and the identification of microbial communities indigenous to natural soil and water environments, and the discovery of microorganisms of potential value for use in biotechnology.

The present invention for the first time allows for the cultivation, selective enrichment and comprehensive biochemical characterization of microorganisms in their natural environments. Its technology:

(a) combines the following tools/approaches: solid-phase sampling techniques, in situ enrichment and biochemical screening, use of electron donor/acceptor pairs, isotope labeling and massive parallel screening with automated analysis, (b) makes use of in situ microcosm arrays in conjunction with culture-independent microbial community analysis to obtain a comprehensive picture of microbial communities, (c) can provide data for hundreds or even thousands of hypothetical environmental scenarios, thereby allowing one to determine quickly and in an automated fashion the likely rates of environmental change induced by these perturbations, (d) is suitable for linking specific microbes to observed reactions by using computer-assisted subtractive profiling techniques, (e) is fully compatible with existing robotic systems, thereby allowing for rapid and fully automated analysis using chemical, physical, biological, genomic and proteomic analysis techniques, (f) allows one to determine how non-native microorganisms will cope in natural environments when confronted with physical, biological and/or chemical stressors, (g) can be optimized for exclusive in situ applications, ex situ applications, or a combination of the two, and (h) allows for proteomic approaches to be used for rapid and fully automated analysis (e.g., matrix assisted laser desorption/ionization time-of-flight mass spectrometry (MALDI-TOF MS) and protein sequencing of enzymatic digests using tandem mass spectrometry (MS/MS)).

One embodiment of the present invention takes the form of an in situ microcosm array (ISMA) sampler or testing device 1. As shown in FIGS. 1-4, its principal components include: a housing or container 10 having a fluid inlet 12 and outlet 14, a plurality of capillary microcosms 16 situated within this housing, with these capillaries 16 making up what is referred to as a microcosm array, each of these capillaries 16 having an inlet 18 and outlet 20 that are configured so as to allow for fluid flow through the capillaries 16, each of these capillaries contains a filtration material 22 that is selected for its ability to foster microorganism collection in the individual capillaries, upper 24 and lower 26 valve plates having openings 28 that are configured to be alignable with the capillary inlets 18 and outlets 20, a pneumatic cylinder 30 with coupling means 32 and an assortment of springs 34 serves to enable these valves to be moved laterally so as to open or close the capillaries' inlets 18 and outlets 20, gasketing pads 36, 38 serve to prevent leakage from these openings, a pump 40 is connected to the container's inlet 14 and is sized so that it can draw fluid from the environment surrounding the container 16 and push it through the container's inlet 12 and through the capillaries 16, a collecting device or a bladder 42 is connected to the pump's outlet and is used to collect the flow through the container 16, a check valve 44 connected between the pump 40 and bladder 42 prevents backflow of fluid through the container 16, a weight 46 serves to provide ballast for suspending via an umbilical cable 48 the sampler 1 down a suitably drilled well that extends into the region of interest.

The initial ISMA prototype samplers of the present invention were based on commercially available 96-position (8×12) microtiter plate format (e.g., Wheaton Scientific Products); similar 384, 1536 (or more) plate formats could have been used. Each well or "microenvironment" of the initial prototype samplers consisted of a Teflon block with 96 drill holes representing individual microcosm capillaries (1.12 mL; 0.295 inch [diameter]×1 inch [length]).

Figure 1:
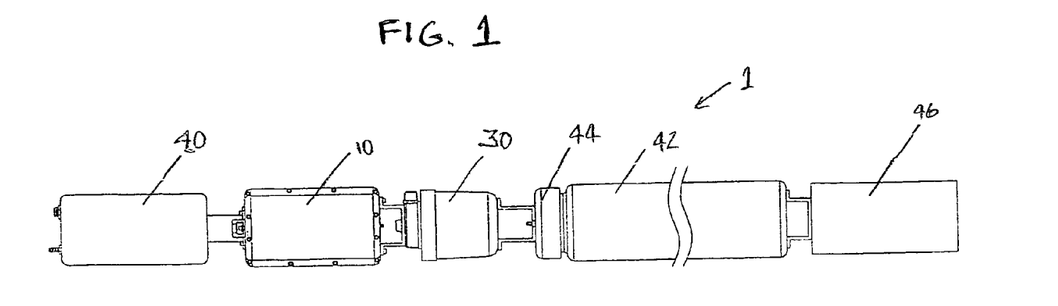
FIG. 1 is a schematic representation of a preferred embodiment of the present invention.
Figure 2:
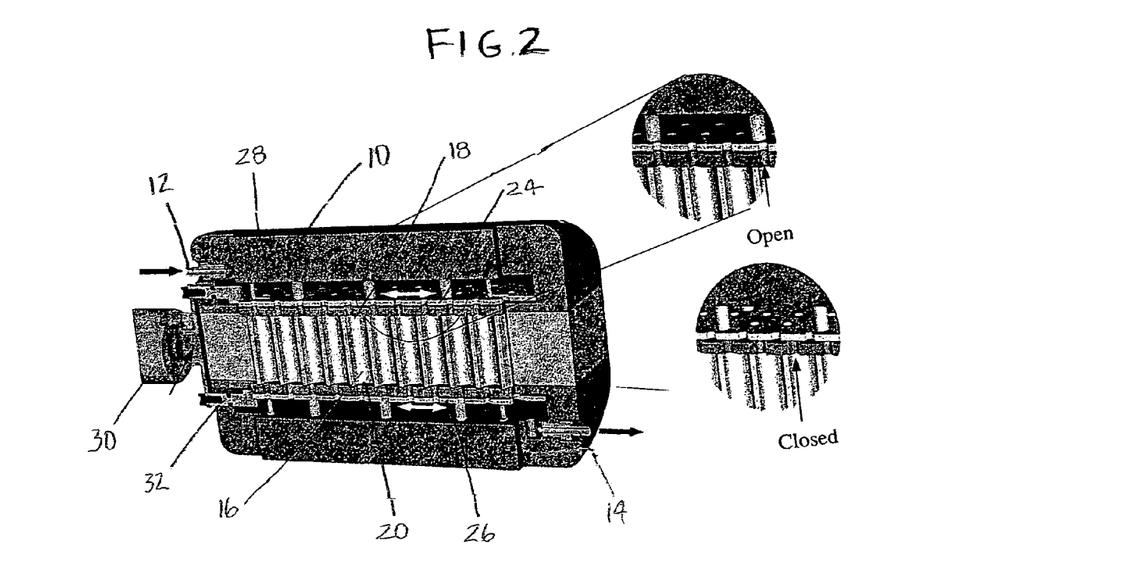
FIG. 2 is a cross-sectional view of the housing shown in FIG. 1, with enlarged representations of a valve plate adjacent to capillary inlets in both their open and closed positions.
Figure 3:
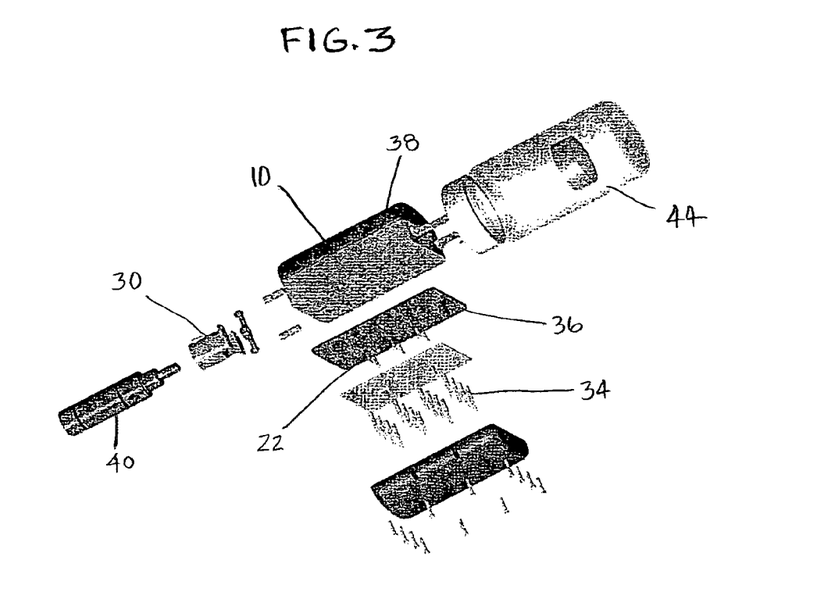
FIG. 3 is an exploded view showing a valve plate of FIG. 1 and the components that are used to cause it to move laterally to open and close the capillary's inlet.
Figure 4:
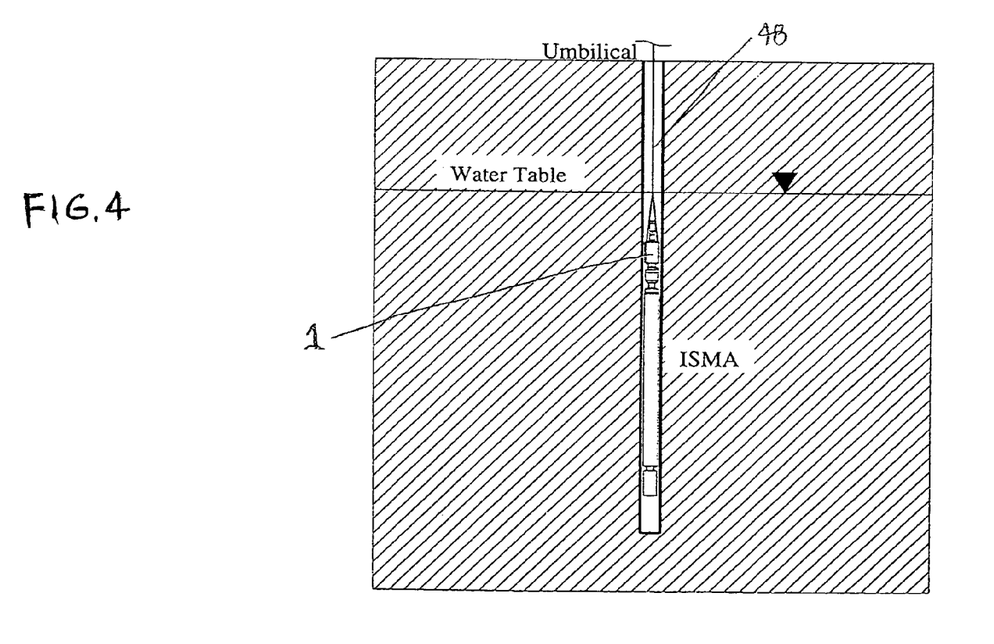
FIG. 4 is a schematic representation of a preferred embodiment of the present invention being extended down a groundwater monitoring well.

The inclusion into the ISMA sampler 1 of a pump 40, closure mechanism valve plates 24, 26, and semi-permeable membranes allows one to first inoculate and then incubate the device in the environment without removing (and potentially harming) the resident microbes from their natural environment. Pump configurations other than those shown in the drawings include, but are not limited to, multi-channel pumps and pump arrays that deliver fluids to the inlet of one or more individual microcosm capillaries.

The ISMA sampler 1 of the present invention can be equipped with a collecting device or a bladder 42. Fluid flowing through the array exits the container and is collected in the bladder. Displacement of air from the collection device may be desirable, and can be achieved by inclusion in the collection device of a bleed valve allowing air to escape via a piece of tubing rising along the umbilical cable to a location some distance above the fluid intake.

As the fluid flows through the device, microorganisms and chemicals can be trapped in the capillary microcosms 16. When the collection device is full, a float can trip power to the pump and actuate the valve plates 24, 26 of the closure mechanism, thereby sealing the array. Immediately, or after an additional incubation period in batch mode, the device 1 can be removed from the environment for further analysis.

The ISMA sampler 1 of the present invention can be designed for reuse. For this purpose, the invention can be equipped with a means allowing for rapid exchange of microtiter plates.

Exchangeable microtiter plates can be manufactured to allow for long-term storage prior to use. For this purpose, the content of customized microtiter plates can be lyophilized and vacuum sealed. Breaking of the vacuum and rehydration of the microtiter content will ready the device for testing. Microtiter contents include, but are not limited to, a means for containing a specified test substance, a test compound, and a test organelle or microorganism.

The ISMA sampler 1 of the present invention can be equipped with a means for capturing microorganisms and chemicals of interest. Such a means can be chosen from the group comprised of sorption, precipitation, sedimentation, coagulation, filtration, straining, extraction, chromatography, affinity separation, size exclusion separation, passive attachment to presented surfaces, and active attachment to presented surfaces.

The ISMA sampler 1 of the present invention can be equipped with microfluidic systems allowing for delivery of small liquid volumes and defined quantities of organelles to the test chamber prior to physical and/or chemical containment of the captured specimens via barriers that are either non-permeable, semi-permeable or completely permeable for chemical compounds. This aspect allows one, for example, to culture uncultivated or "non-culturable" bacteria to numbers sufficiently large to perform biochemical characterization and identification.

This sampler also may be adapted for studying the fate of either beneficial or hazardous chemical agents in natural environments. In this application, the sampler 1 is modified to reflect as closely as possible within each test compartment or microcosm the physical, chemical and biological environment of interest (e.g., flow-through cells equipped with local sediment etc.). Test chemicals are included in the sampler prior to its deployment and diffuse from within the sampler into the ambient fluid. Following interaction with the local environment, all chemicals are captured in the bladder.

This sampler also may be adapted for studying the fate of either beneficial or hazardous biological agents in natural environments. In this application, the sampler 1 is modified to reflect as closely as possible within each test compartment or microcosm the physical, chemical and biological environment of interest (e.g., flow-through cells equipped with local sediment etc.). Test organisms are inoculated into the sampler prior to its deployment and the sampler is incubated in situ allowing for interaction of the test organisms or species with the environment without allowing for its release.

Modification of the sampler's closure valve plates 24, 26 allows for sequential opening and closing of its microcosm compartments. Real-time and monitoring equipment (pH, Eh, temperature, DO, etc.) can be added to the sampler 1 to increase functionality and to trigger reactions at specific points in time selected by changes in the target environment (e.g., heavy rainfall events). Use of radio frequency signaling and remote controls can replace the standard umbilical cord 48 that is used to communicate with the sampler 1, and to determine the chemical change occurring during incubation.

It should be noted that the design of the device can be altered to allow deployment of the device in environments featuring extreme conditions including, but not limited to, extreme pH, temperature, pressure, radiation, gravity conditions different from that of planet Earth, etc. Additionally, many types of microfluidics, filters, sorbent materials, semipermeable membranes and alternative closure mechanisms may be integrated into the sampler to separate in time its inoculation from the incubation period that allows chemical change to take place within the sampler 1.

It should further be noted that the method and device can be used for bioprospecting and environmental monitoring in any fluid-containing environment including, but not limited to, subsurface environments, surface environments, saturated environments in space, and macroorganisms dead or alive.

Optical and/or electrical detection systems may be incorporated in the microfluidic configurations of the sampler 1 to seal individual microcosms as soon as a single cell has been delivered to the microcosms, thereby greatly increasing the success rate of isolating novel microorganisms.

For example, optical sensors detecting the entry of individual microorganisms into the device, can trigger translation of the valve plates to move from the "open" position into the "closed" position. Different surfaces can be presented in the "closed" position. If the presented surface is impermeable to the microorganism and the flow of water, complete confinement is achieved. If the presented surface is a semi-permeable membrane, water can continue to flow through the device whereas the microorganism is held in confinement.

The present invention's approach for the identification of microorganisms involves looking for gene expression products (i.e., proteins) as well as for their characteristic DNA sequences. For example, ribosomal proteins are used as biomarkers to identify microorganisms by MALDI TOF MS.

For the rapid automated detection of specific microorganisms by MALDI TOF MS, individual microcosms can be configured to support only the growth of specific microorganisms. This is achieved by including in the microcosm chemicals that foster the growth of the target microorganism while suppressing the growth and survival of non-target microorganisms. For example, a combination of selective substrates and antibiotics can serve for this purpose. This type of selective culturing, a common strategy in the microbiology laboratory, is now being performed in situ. By doing so, growth of specific microorganisms and expression of key biomolecules can be achieved. Selective in situ culturing of specific microorganisms then allows for direct detection and identification of these biological agents by mass spectrometry. It makes unnecessary the need for extensive sample preparation and cleanup because of the enhanced signal-to-noise characteristics of the enriched sample.

This in situ cultivation technique can also be used to determine the metabolic and catabolic activity of microorganisms in situ. For this purpose, the presented chemicals can contain isotopic labels such as isotopes of carbon-12 (e.g., $^{13}C$, $^{14}C$).

Use of the invention in conjunction with SIP and nonculture-dependent microbial community profiling tools is another important application.

Figure 5A:
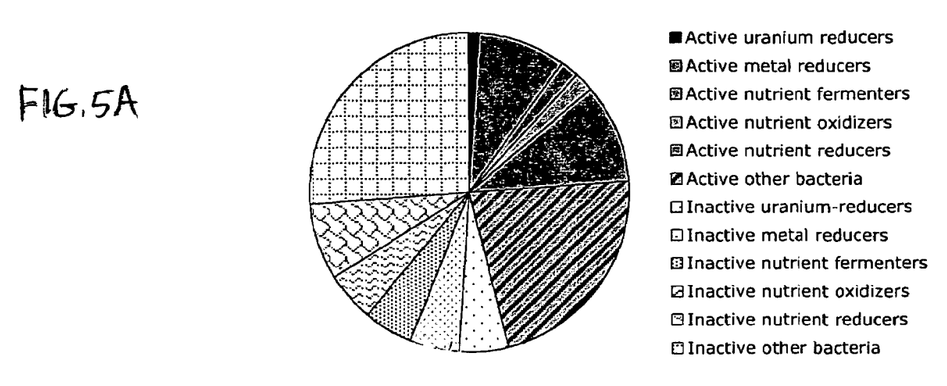
FIGS. 5A-5C illustrate the utility of the present invention for microbial community analysis at an uranium contaminated site. Conventional microbial community analysis produces a picture as shown in FIG. 5A. The present invention allows for the determination of 96 or more community profiles determined under various environmental conditions as shown in FIG. 5B. Environmental conditions in the sampler of the present invention allow for the selective enrichment of pollutant-degrading bacteria; some of these may be detected for the first time, as shown in FIG. 5C.
Figure 5B:
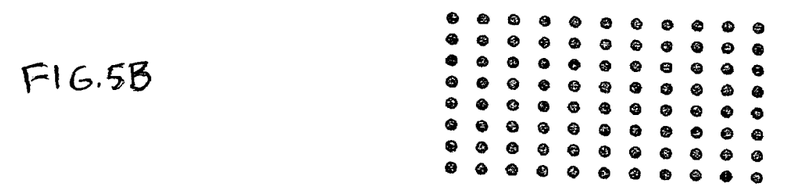
Figure 5C:
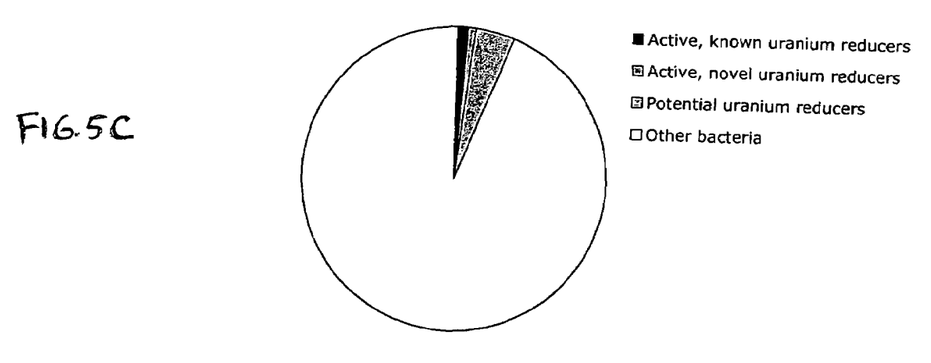

The advantages of this process are illustrated in FIGS. 5A-5C as applied to the bioremediation of saturated subsurface environments containing uranimum. Conventional microbial community analysis produces a picture as shown in FIG. 5A; the technique detects the presence of all bacteria; however, it does not provide information on their metabolic activity. The use of isotope-labeled nutrients can reveal which of the detected microorganisms are metabolically active (right half of the community shown in FIG. 5A).

Use of the ISMA sampler 1 allows for the determination of 96 or more community profiles determined under various environmental conditions (e.g., a screening study in which uranium is being presented at various concentrations), see FIG. 5B. Computational analysis of the resulting data using subtractive community profiling allows one to identify important pollutant-transforming microorganisms within the large group of active microorganisms (not all metabolically active bacteria are partaking in the bioremediation process).

Environmental conditions in the sampler allow for the selective enrichment of pollutant-degrading bacteria; some of these may be detected for the first time, see FIG. 5C. Under appropriate conditions, a poorly represented population may be enriched to a level allowing for MALDI TOF MS-based detection/identification.

To discern which of the potentially relevant microorganisms detectable at a given site are performing a desired reaction, SIP methods may be used. Stable isotopes are used as chemical reporters to help to discriminate metabolically active bacteria from dormant or dead community members and from those performing functions unrelated to desired bioremediation or biostimulation.

Isotope labeled substrates (e.g., $^{13}C$-labeled acetate) may be used as chemical reporters of biotransformation activity in a miniaturized, field-deployable, down-well ISMA. As previously mentioned, each of these devices holds different, physically separated test environments, "test wells" or capillary microcosms.

The method of the present invention begins with placing a suitably configured ISMA in the environment to be examined (e.g., a contaminated, underground site which is accessed by a monitoring well). Once the ISMA has been lowered into a monitoring well to the desired depth, it is triggered from the surface via an electrical signal conducted by a wire (or via other means such as a programmed build-in mechanism). Triggering of the device exposes each of the "test wells" to the flow of groundwater. Microorganisms suspended in the groundwater attach themselves to the presented surfaces and become trapped in the device. Additional free-living microbes become trapped once the device receives the signal to close again.

Some of the test wells may include the contaminant of concern. Individual test wells may also contain, as previously mentioned, one stable-isotope labeled nutrient for determining its effect on microbial growth and activity. The now closed device is incubated in situ to allow for growth of microorganisms on the labeled substrates.

During this incubation period, all bacteria directly or indirectly involved in the utilization of isotope-labeled electron donors become enriched in isotope-labeled DNA. Following retrieval of the tool from the well, microorganisms are collected from the device and their isotope-labeled, higher-density DNA is separated from background DNA by density-gradient centrifugation. This higher-density DNA (and the non-labeled DNA) is then analyzed using known molecular techniques.

Oligonucleotide microarrays serve to identify/enumerate target-specific organisms whereas clone libraries may be used to identify novel, uncultured microorganisms. The device may, ideally, be used in conjunction with commercially available robotics for automated extraction of DNA.

The extent of microbially induced corrosion of metals/radionucliudes may be measured optically by scanning a metal surface placed within the ISMA with a laser; alternatively, contaminant biotransformation may be detected biochemically via addition of a dye/reporter or electrochemically via measurement of electrical resistance. Measurements can be performed real time in situ or post-deployment via analysis of the capillary content, the bladder content, and sorbent materials that were integrated in the device and had an opportunity to chemically interact with fluid drawn into the device.

If uranium is the contaminant of concern, analysis of an uranium-coated surface allows for determining the extent of uranium reduction and the calculation of pollutant removal rates occurring under in situ conditions.

As previously mentioned, test wells of the device also may be equipped with a matrix allowing for the slow, continuous release of chemicals (e.g., external carbon and energy sources; other nutrients; conditioning agents such as pH or redox agents). The matrix may be a polymer or a membrane vesicle containing the nutrient in question. Diffusion characteristics of the matrix/membrane are selected to achieve different nutrient levels in each of the test wells if desired. Presented nutrients may be added in solid, liquid or gaseous state. Energy sources may be presented in the presence and absence of pollutant coating.

Some of the test wells may be configured for continuous flow-through operation in situ. Flow through the device may be passive or active. In active devices, a small pump 40 facilitates groundwater movement whereas tubing of various length and configuration is used to prevent the effluent of one test well from becoming the influent of another.

Figure 6:
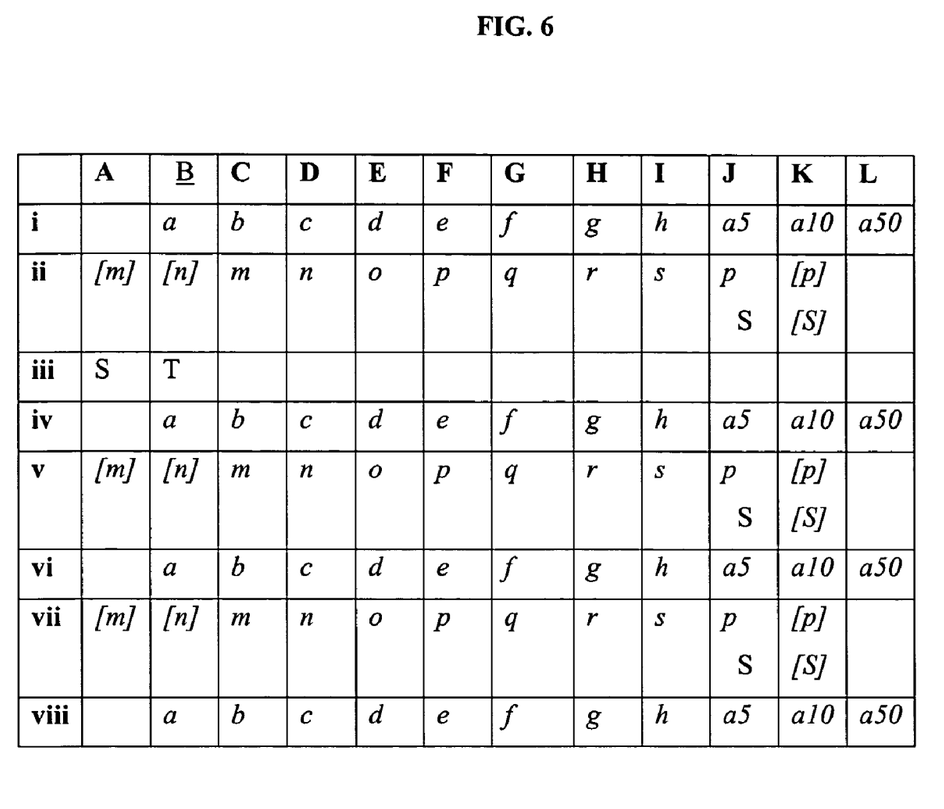
FIG. 6 shows one possible configuration of a 96-well microtiter plate configured for environmental monitoring and bioprospecting at a hypothetical site containing groundwater contaminated with fuel hydrocarbons from a point source, and dibenzofuran, and the pyrethroid degradate 3-phenoxybenzoic acid (3-POB) from non-point sources.

FIG. 6 shows one possible configuration of a 96-well microtiter plate configured for environmental monitoring and bioprospecting at a hypothetical site containing groundwater contaminated with fuel hydrocarbons from a point source, and dibenzofuran, and the pyrethroid degradate 3-phenoxybenzoic acid (3-POB) from non-point sources. The 96 microcosm capillaries are aligned in parallel in 12 columns ("A" through "L") and 8 rows ("i" through "viii"). In the microtiter plate customized for this site, all capillaries contain a webbing material for capturing microorganisms. Near the inlet in the front half of each microcosm capillary, the webbing material contains noble agar beads serving as an inert diffusive matrix. Near the outlet in the back half of each microcosm capillary, the webbing material contains sorbent beads to which contaminants can sorb. Capillary Ai does not contain any test substances or microorganisms. When the ISMA is deployed in flow-through mode in the contaminated aquifer, chemical conditions reported for microcosm Ai by real-time sensors are reflective of ambient groundwater quality. Similarly, chemical analysis of the sorbent beads contained in microcosm Ai will yield a time-integrated measure of the contaminant mass that passed through the microcosm during deployment in local groundwater. Following capture of microorganisms in the ISMA during flow-through mode, the valve plates are translated to close the device. Real-time sensing data for microcosm Ai, now incubated in batch mode, will inform on the kinetics of pollutant degradation under ambient conditions (intrinsic bioremediation rate; loss of contaminants as a function of time).

If the groundwater passing through microcosm Ai is anaerobic (ISMA Deployment Location 1; immediately downgradient of the leaking fuel tank), biodegradation of fuel hydrocarbons will be slow and incomplete. In order to accelerate the biodegradation process, a number of electron acceptors can be considered. Rapid, simultaneous screening of common electron acceptor compounds is achieved within the ISMA in microcosms in row "i" (Bi through Ii). Individual electron acceptor compounds presented in these microcosms reflect a redox gradient ranging from highly oxidizing to more reducing conditions: Bi, oxygen releasing formulation (a); Ci, nitrate (b); Di, nitrite (c); Ei, manganese oxide ($MnO_2$) (d); Fi, iron ($Fe^{(III)}$) (e); Gi, uranium ($U^{(VI)}$) (f); Hi, chromium ($Cr^{(VI)}$) (g); and Ii, sulfate (h). By incubating the ISMA in batch mode with these electron acceptors present in excess concentrations relative to the contaminants, real-time sensors from microcosms Bi through Ii will directly report on the results of this screening study of biodegradation of fuel hydrocarbons under a variety of redox conditions. Once the optimal redox conditions have been identified, it is of interest to determine what dosage is needed. Assuming that pollutant turnover was most rapid in the microcosm Bi containing oxygen-releasing formulation (a), the optimal dosage of this "nutrient" can be inferred by comparing the degradation rates obtained in microcosms containing 5-fold (Ji), 10-fold (Ki), and 50-fold (Li) higher levels of oxygen-releasing formulation relative to microcosm Bi. Thus, data obtained with the top row of microcosms already has yielded estimates of intrinsic and enhanced biodegradation rates, and resulted in the identification of the most favorable redox conditions, as well as the optimal dosage of electron acceptors. Other nutrients and conditions can be screened in a similar fashion.

The effectiveness of chemical treatment for the cleanup of groundwater at the fuel spill site is investigated using second-row microcosms Aii through Fii. The removal of hydrocarbons by Fenton's reagent (m) and potassium permanganate (n) is evaluated. In the configuration shown, microcosm Aii and Bii are covered with an inert membrane filter that allows liquid to flow through the capillaries whereas the entry of microorganisms is prevented. Sequential incubation of these microcosms in flow-through and batch mode allows for a direct in situ comparison of the two oxidation agents or chemical treatment strategies. Microcosms Cii and Dii are not sealed with an inert membrane but are otherwise identical to Aii and Dii, respectively. Direct comparison of chemical data from these two pairs of microcosms allows one to evaluate whether biotransformation and chemical oxidation processes can occur simultaneously.

For site assessment purposes, identical ISMA samplers will be deployed at various locations at a given site. For the hypothetical site discussed here, Deployment Location 2 is far downgradient of the release site, outside of the hydrocarbon contaminant plume. In this location, groundwater is expected to be aerobic and will contain only contaminants from non-point sources. In this case, these are represented by 3-phenoxybenzoic acid and dibenzofuran.

Seeding of the ISMA sampler with viable microorganisms (hydrated or lyophilized) is useful for evaluating bioaugmentation and environmental risk assessment of pathogenic and non-pathogenic microorganisms. The customized ISMA sampler considered here, has been seeded with 10 million microorganisms of a particular kind per microcosm (Eii through Hii): Eii, *Escherichia coli* O157:H7, a pathogen (o); Fii, *Sphingomonas wittichii* RW1, a dibenzofuran-degrading bacterium (p); Gii, *Pseudomonas pseudoalcaligenes* strain POB310, a 3-phenoxybenzoate-degrading microorganism (q); and Hii, *Pseudomonas* sp. strain B13-D5, a genetically engineered microorganism (r) specifically designed to degrade 3-phenoxybenzoic acid rapidly and completely.

One way of evaluating the survival of these microbes in the target environment, is to enumerate culturable cells following deployment, incubation, and retrieval of the ISMA sampler. The effect of environmental conditions on the survival of seeded microorganisms can be evaluated by comparing microbial counts obtained for identical microcosms incubated in different locations, e.g. the survivability of the pathogenic E. coli strain at Deployment Locations 1 and 2 can be assessed by comparing the two viable counts obtained for microcosm Eii.

Strain RW1 is a naturally occurring bacterium capable of utilizing dibenzofuran as a carbon and energy source. Its detection in the dibenzofuran-contaminated aquifer could indicate an intrinsic bioremediation potential for this chemical at the site. One detection technique for the microorganism is the use of strain-specific PCR primers and probes. Alternatively, the bacterium can be detected by mass spectrometry. However, if strain RW1 is present in site groundwater, its environmental density will be orders of magnitude lower than required for this task. The ISMA compartment Iii is configured to overcome this limitation. Microcosm Iii contains the selective substrate dibenzofuran (s). During in situ incubation of microcosm Iii in batch mode in aerobic groundwater, strain RW1 is allowed to increase in density from non-detectable to detectable levels by growing at the expense of dibenzofuran. The presence of dibenzofuran serves two purposes. First, it allows the target bacterium (RW1) to grow to levels sufficiently high for detection by mass spectrometry (>10^7 cells total per microcosm); second, it increases the expression of dioxin dioxygenase, a characteristic enzyme serving as the target for mass spectrometric identification of RW1. The combined effect of in situ growth of RW1 and induction of high levels of dioxin dioxygenase in cells of RW1 is an enhanced signal-to-noise ratio during mass spectrometric analysis (in situ biomarker amplification): levels of dioxin dioxygenase are high relative to the background of non-target proteins contained in the mixture of environmental microorganisms.

Under starvation conditions, microorganisms may divide several times to form ultra-microbacteria; in these instances, viable cell counts indicate bacterial growth (proliferation) whereas, in actuality, the local bacterial population is on the brink of extinction. The ISMA can assist in distinguishing between true microbial growth and the starvation effect described above. This goal is achieved with microcosm Jii that contains the microorganism RW1 (p) and a stable isotope labeled ($^{13}$C-containing) analog of dibenzofuran (S). Following incubation of the microcosm in situ, its content can be analyzed by mass spectrometry. Successful in situ growth of strain RW1 will be revealed by the detection of a mixture of light (non-labeled) and heavy (isotope-labeled) peptides of the dioxin dioxygenase; the ratio of heavy isotopes-to-low isotopes detected by mass spectrometry informs about the rate of $^{13}$C-dibenzofuran uptake in situ, a measurement that cannot be obtained in field tests because the massive injection of isotope-labeled compounds is cost-prohibitive and faces regulatory obstacles.

Microcosm Kii can be used to illustrate the benefit of data normalization achievable by incorporation of standard microcosms into the ISMA sampler. Microcosm Kii is identical to Jii but sealed with an inert semi-permeable membrane that excludes the entry of indigenous groundwater microorganisms. This microcosm can serve as a benchmark for metabolic activity at the sampling location. For example, when ISMA samplers are deployed year-round in the shallow aquifer of Deployment Location 2, the turnover of $^{13}$C-dibenzofuran and assimilation of $^{13}$C will undergo seasonal fluctuation as a result of subtle changes in water temperature. The direct comparison of datasets obtained with identically configured ISMAs deployed at different points in space and time can be achieved via normalizing the results using the readouts from standard microcosms such as Kii. By doing so, results for the microcosms in row "i" obtained over the course of the year may collapse into a single value. If they do not, this may indicate a relative loss of hydrocarbon degradatation activity in the aquifer.

Following deployment and retrieval of the ISMA sampler, the microbial community of each capillary microcosm can be analyzed using culture-independent techniques such as DNA extraction, amplification of the 16S RNA genes, separation of amplification products by denaturing gradient gel electrophoresis (DGGE), and sequencing of bands followed by phylogenetic sequence analysis. Linking microbial function and phylogeny is an important goal. Subtractive community profiling, i.e., eliminating irrelevant information from large datasets by subtracting multiple datasets from each other, represents one possible way of identifying within a large number of microorganisms the ones that are responsible for a biochemical process of interest (FIG. 5A-C).

Another approach to achieve this goal is the use of stable isotope probing. The ISMA technology greatly enhances the utility of this technique for three reasons. One, it facilitates inexpensive SIP analysis by minimizing the volume of liquid required to be spiked with expensive isotope labeled compounds. Two, it allows for batch incubation which increases the labeling efficiency dramatically when compared to labeling in open systems. Three, it avoids the regulatory hurdles associated with injecting isotope-labeled compounds into target environments during field tests.

The utility of the ISMA technology for use with SIP is illustrated by microcosm Aiii and Biii. Microcosm Aiii is identical to microcosm Iii except for the fact that the dibenzofuran contained therein is labeled with $^{13}$C. Following use of the ISMA sampler in Deployment Location 2, culture-independent microbial community analysis of microcosm Iii will yield a large number of DNA sequences some of which may correspond to naturally occurring dibenzofuran-degrading microorganisms. These cannot easily be distinguished from the large background of other bacteria, however. Analysis of microcosm Aiii by SIP will aid in their identification. Following in situ deployment of the ISMA sampler, DNA is being extracted from microcosm Aiii. The obtained DNA is spun in a cesium chloride density gradient to separate $^{12}$C-DNA from $^{13}$C-DNA. Analysis of $^{13}$C-DNA by PCR, DGGE and DNA sequencing will reveal the identity of microorganisms involved in the turnover of dibenzofuran.

Assuming that a sequence corresponding to a single $^{13}$C-labeled microorganism is detected, and that its DNA sequence information is different from that of RW1, then a novel microorganism capable of metabolizing dibenzofuran has been discovered with the ISMA technology. If the $^{13}$C-labeled metabolites detectable in microcosm Aiii are different from those reported for strain RW1, then a novel biochemical process has been detected, whereas the metabolite itself may represent a novel natural product of potential commercial value. Similarly, detection of significant fungal growth in microcosm Biii (containing $^{13}$C-labeled sucrose; T) and concurrent lack of detection of $^{13}$C-labeled DNA corresponding to Gram-positive bacteria can reveal the presence of a fungal natural product suitable for the treatment of Gram-positive infections in animals and humans.

Replicates of individual test systems can be distributed randomly within the 12×8 microtiter format. Analysis of replicate systems informs about the precision of the experimental data obtained. Replicates shown in FIG. 6 include: for Ai-Ciii to Liii, for row i-rows iv, vi and viii, for row ii-rows v and vii.

The test systems disclosed herein will report on intrinsic (bioremediation) biocorrosion potential and rates. Computational analysis of the resultant data sets using subtractive profiling adds a hitherto unattained discriminatory power to the analysis of both microbial community composition and function in subsurface environments.

The technology of the present invention uses various proven techniques and technologies in a novel and non-obvious way to achieve the desired goal: the rapid automated analysis of field samples for microbial community composition, degradative potential, and degradative activity under prevalent conditions and under those conditions that may be created in situ to accelerate the bioremediation process. Techniques/technologies incorporated in the present invention include:

1) Down-well tools for sampling for monitoring wells
2) Microtiter-plate testing and fully automated analysis
3) Slow-release compounds for continuous release of microbial nutrients
4) Membrane technology for delivery of nutrients
5) Micro fluidics
6) Laser detection of microbially-induced corrosion
7) Automated DNA extraction
8) Isotope labeling of microorganisms
9) Density gradient analysis for separation of high-density labeled DNA
10) Microbial community analysis using microarrays and bioinformatics
11) Subtractive community profiling for identification of relevant microorganisms
12) Sorbent materials that can be analyzed to determine the chemical composition of fluid in the individual test compartments.

The usefulness of the present invention's analytical methods can be further aided by: (a) development of mass spectrometric techniques for the identification of microorganisms in mixed cultures, and (b) the generation of microorganism-identification database software and search algorithms for interpreting MALDI TOF mass spectra of ribosomal biomarkers and microorganisms.

Speed and ease of analysis for the present invention is achieved by replacing molecular-genetic analyses with other more convenient measurement techniques suitable for discerning isotope distributions (e.g., use of MALDI-TOF MS and bioinformatics database searches for automated microorganism identification). Sample processing uses commercially available robotics (e.g., Amersham Biosciences robotics) and tools for rapid sample cleanup and processing (e.g., Gyrolab MALDI SP1 etc.) in conjunction with enzymatic digestion steps (e.g., trypsin digestion).

Central laboratory facilities are recommended for analyzing samplers deployed in situ. This allows for automated analysis and for a high degree of standardization. Standardized analysis in turn improves measurement precision and allows one to determine the systematic biases of the technique (due to "bottle effects") that may limit measurement accuracy. Once identified, these biases can be accounted and corrected for thus enabling one to predict—with high accuracy and precision—the environmental change to be observed following engineering interventions.

Proof-of-concept experiments with components of the testing device of the present invention have demonstrated that:

1. Informative microbial community data can be obtained with nonculture-dependent tools using analysis of conventional groundwater samples and bioremediation microcosms.

2. The screening of electron acceptors and donors in microcosms adds discriminatory/predictive power for microbial community profiling.

3 Integration of stable isotope-labeled electron donor compounds into the microcosm design aids in the identification of metabolically active microorganisms.

4. Adaptations of mass spectrometric analysis of microorganism-specific proteins can be used to identify microorganisms in environmental mixed cultures directly without the need for time and labor intensive separation techniques.

5. Adaptation of microorganism-identification algorithms contained in the existing protein-identification database software allows for the analysis of mixed cultures.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention.

I claim:

1. A testing device for environmental monitoring and bioprospecting for microorganisms within a specified environment, said device comprising:

a plurality of physically separated, test microcosms that are so configured as to allow for fluid flow on a path through said microcosms, wherein the test microcosms are holes in a solid block of material, wherein each microcosm is configured to allow fluid flow from an inlet end to an outlet end while retaining microorganisms within the microcosms defined by the solid block, a housing for containing and protecting said test microcosms as they are placed in an environment, said housing further providing for flow of fluid from said environment to enter and flow through said microcosms, and valves for covering said fluid flow paths through said microcosms so as to regulate the flow through said microcosms.

2. A testing device as recited in claim 1, wherein said plurality of microcosms being configured so as to allow for automated analysis of said microcosms using commercially available robotics.

3. A testing device as recited in claim 2, further comprising:
a pump for causing fluid flow from said environment and through said microcosms,
a collecting device for collecting and retaining said fluid flowing through said microcosms, and
a check valve downstream from said microcosms for preventing backflow of said fluid into said microcosms.

4. A testing device as recited in claim 3 further comprising at least one of said microcosms configured for fostering the collection of said microorganisms that enter said microcosm.

5. A testing device as recited in claim 3 wherein at least one of said microcosms comprises a specified test substance that can diffuse into the fluid flowing through said microcosm.

6. A testing device as recited in claim 3, wherein a test microcosm configured so as to aid in addressing research interests chosen from the group consisting of the identification and linking of the microbial function occurring in said environment to phylogeny, wherein at least one of said microcosms having placed therein an isotope labeled test compound that can be used in conjunction with SIP, identification and linking of the microbial function occurring in said environment to phylogeny, wherein at least one of said microcosms having placed therein an isotope labeled test compound that can be used in conjunction with mass spectrometry, survival in said environment of a specified microorganism, herein at least one of said microcosms having placed therein said specified microorganism, fate in said environment of a specified, genetically engineered microorganism, wherein at least one of said microcosms is configured to contain said genetically engineered microorganism, fate in said environment of a specified pathogen, wherein at least one of said microcosms is configured to contain said pathogen, for a specified process in said environment, the effectiveness of specified, varying test substances for their ability to accelerate said process, wherein said test substances are added to said microcosms, identification of microorganisms indigenous to said environment that are responsible for a desired bioremediation process in said environment, effectiveness of said varying bioremediation strategies for said environment, wherein said microcosms are configured to be representative of said varying bioremediation strategies, effectiveness of said varying bioaugmentation strategies for said environment, wherein said microcosms are configured to be representative of said varying bioaugmentation strategies, effectiveness of said varying chemical treatment strategies for said environment, wherein said microcosms are configured to be representative of said varying chemical treatment strategies, intrinsic transformation rates in said environment when said environment is contaminated with a specified contaminant, enhanced transformation rates in said environment when said environment is contaminated with a specified contaminant, wherein specified nutrients are added to said microcosms, analysis of a microbial community indigenous to said environment, proteomic analysis of a microbial community indigenous to said environment, discovery within said environment of novel microorganisms of potential commercial value, discovery within said environment of novel biochemical processes of potential commercial value, discovery within said environment of a novel natural natural of potential commercial value, normalization of test results achieved with said device for differences between when and where said tests are conducted, wherein at least one of said microcosms is configured to serve as an internal standard to which said results can be normalized, identification of a chemical for enhancing a signal-to-noise ratio in the mass spectrometric analysis of a specified microorganism, wherein at least one of said microcosm configured to foster growth of said microorganism while limiting growth and survival of other, non-specified microorganisms, determination of a fate of a specified compound in said environment for chemical risk assessment, wherein at least one of said microcosms having placed therein said compound, determination of a effect of a specified compound on a microbial community of said environment for chemical risk assessment, wherein at least one of said microcosms having placed therein said compound, determination of a fate of a specified microorganism for biological risk assessment, wherein at least one of said microcosms having placed therein said microorganism, determination of an effect of a specified microorganism on a microbial community of said environment for biological risk assessment, wherein at least one of said microcosms having placed therein said specified microorganism, determination, for environmental monitoring purposes of an effect of a specified agent in said environment, wherein at least one of said microcosms having placed therein said agent, said placement being such that said agent is retrievable from said microcosm, determination, for risk assessment purposes of an effect of a specified agent in said environment, wherein at least one of said microcosms having placed therein said agent, said placement being such that said agent is retrievable from said microcosm, determination, for environmental treatment purposes of the effect of a specified agent in said environment, wherein at least one of said microcosms having placed therein said agent, said placement being such that said agent is retrievable from said microcosm, determination, for environmental monitoring purposes of an effect of a specified agent in said environment, wherein at least one of said microcosms having placed therein said agent and said device being configured such that said fluid from the environment that comes into contact with said agent in said microcosm is retrievable, determination, for risk assessment purposes of an effect of a specified agent in said environment, wherein at least one of said microcosms having placed therein said agent and said device being configured such that said fluid from the environment that comes into contact with said agent in said microcosm is retrievable, determination, for environment treatment purposes, of an effect of a specified agent in said environment, wherein at least one of said microcosms having placed therein said agent and said device being configured such that said fluid from the environment that comes into contact with said agent in said microcosm is retrievable, determination, for environmental monitoring purposes of an effect of a specified biochemical process in said environment, wherein said microcosm covering means being configured so that a duration of said process in said microcosm is controllable, elucidation of the in situ metabolic activity of a specified microorganism, wherein at least one of said microcosms having placed therein an isotope labeled test compound which is to be analyzed for a ratio of light (non-labeled) and heavy (labeled) biomarkers of said microorganism, and detection of a specified microorganism in said environment, wherein at least one of said microcosms having placed therein a test compound suitable for increasing a signal-to-noise ratio of a characteristic biomarker of said microorganism during mass spectrometric analysis following in situ biomarker amplification.

7. A testing device as recited in claim 3, further comprising a remote control for remotely controlling the operation of said valve for covering said microcosm fluid flow paths and said pump for causing fluid flow through said microcosms.

8. A testing device as recited in claim 2 further comprising at least one of said microcosms configured for fostering the collection of said microorganisms that enter said microcosm.

9. A testing device as recited in claim 2 wherein at least one of said microcosms having comprises a specified test substance that can diffuse into the fluid flowing through said microcosm.

10. A testing device as recited in claim 2, wherein a test microcosm configured so as to aid in addressing research interests chosen from the group consisting of:

identification and linking of microbial function occurring in said environment to phylogeny, wherein at least one of said microcosms having placed therein an isotope labeled test compound that can be used in conjunction with stable isotope probing (SIP), identification and linking of the microbial function occurring in said environment to phylogeny, wherein at least one of said microcosms having placed therein an isotope labeled test compound that can be used in conjunction with mass spectrometry, survival in said environment of a specified microorganism, herein at least one of said microcosms having placed therein said specified microorganism, fate in said environment of a specified, genetically engineered microorganism, wherein at least one of said microcosms is configured to contain said genetically engineered microorganism, fate in said environment of a specified pathogen, wherein at least one of said microcosms is configured to contain said pathogen, for a specified process in said environment, effectiveness of specified, varying test substances for their ability to accelerate said process, wherein said test substances are added to said microcosms, identification of microorganisms indigenous to said environment that are responsible for a desired bioremediation process in said environment, effectiveness of varying bioremediation strategies for said environment, wherein said microcosms are configured to be representative of said varying bioremediation strategies, effectiveness of varying bioaugmentation strategies for said environment, wherein said microcosms are configured to be representative of said varying bioaugmentation strategies, effectiveness of varying chemical treatment strategies for said environment, wherein said microcosms are configured to be representative of said varying chemical treatment strategies, intrinsic transformation rates in said environment when said environment is contaminated with a specified contaminant enhanced transformation rates in said environment when said environment is contaminated with a specified contaminant, wherein specified nutrients are added to said microcosms, analysis of a microbial community indigenous to said environment, proteomic analysis of a microbial community indigenous to said environment, discovery within said environment of novel microorganisms of potential commercial value, discovery within said environment of novel biochemical processes of potential commercial value, discovery within said environment of a novel natural product of potential commercial value, normalization of test results achieved with said device for differences between when and where said tests are conducted, wherein at least one of said microcosms is configured to serve as an internal standard to which said results can be normalized, identification of a chemical for enhancing a signal-to-noise ratio in a mass spectrometric analysis of a specified microorganism, wherein at least one of said microcosm configured to foster the growth of said microorganism while limiting the growth and survival of other, non-specified microorganisms, determination of a fate of a specified compound in said environment for a chemical risk assessment, wherein at least one of said microcosms having placed therein said compound, determination of an effect of a specified compound on a microbial community of said environment for chemical risk assessment, wherein at least one of said microcosms having placed therein said compound, determination of a fate of a specified microorganism for biological risk assessment, wherein at least one of said microcosms having placed therein said microorganism, determination of an effect of a specified microorganism on a microbial community of said environment for biological risk assessment, wherein at least one of said microcosms having placed therein said specified microorganism, determination, for environmental monitoring purposes of an effect of a specified agent in said environment, wherein at least one of said microcosms having placed therein said agent, said placement being such that said agent is retrievable from said microcosm, determination, for risk assessment purposes of an effect of a specified agent in said environment, wherein at least one of said microcosms having placed therein said agent, said placement being such that said agent is retrievable from said microcosm, determination, for environmental treatment purposes of an effect of a specified agent in said environment, wherein at least one of said microcosms having placed therein said agent, said placement being such that said agent is retrievable from said microcosm, determination, for environmental monitoring purposes of an effect of a specified agent in said environment, wherein at least one of said microcosms having placed therein said agent and said device being configured such that said fluid from the environment that comes into contact with said agent in said microcosm is retrievable, determination, for risk assessment purposes of an effect of a specified agent in said environment, wherein at least one of said microcosms having placed therein said agent and said device being configured such that said fluid from the environment that comes into contact with said agent in said microcosm is retrievable, determination, for environment treatment purposes, of an effect of a specified agent in said environment, wherein at least one of said microcosms having placed therein said agent and said device being configured such that said fluid from the environment that comes into contact with said agent in said microcosm is retrievable, determination, for environmental monitoring purposes of an effect of a specified biochemical process in said environment, wherein said microcosm valve being configured so that the duration of said process in said microcosm is controllable, determination, for risk assessment purposes of an effect of a specified biochemical process in said environment, wherein said microcosm valve being configured so that the duration of said process in said microcosm is controllable, determination, for environmental treatment purposes, of an effect of a specified biochemical process in said environment, wherein said microcosm valve being configured so that a duration of said process in said microcosm is controllable, elucidation of a in situ metabolic activity of a specified microorganism, wherein at least one of said microcosms having placed therein an isotope labeled test compound which is to be analyzed for a ratio of light (non-labeled) and heavy (labeled) biomarkers of said microorganism, and detection of a specified microorganism in said environment, wherein at least one of said microcosms having placed therein a test compound suitable for increasing a signal-to-noise ratio of a characteristic biomarker of a microorganism during mass spectrometric analysis following in situ biomarker amplification.

11. A testing device as recited in claim 2, further comprising a remote control for remotely controlling the operation of said valve for covering said microcosm fluid flow paths and said pump for causing fluid flow through said microcosms.

12. A testing device as recited in claim 1, further comprising:
 a pump for causing fluid flow from said environment and through said microcosms,
 a collecting device for collecting and retaining said fluid flowing through said microcosms, and
 a check valve downstream from said microcosms for preventing backflow of said fluid into said microcosms.

13. A testing device as recited in claim 12 further comprising at least one of said microcosms configured for fostering the collection of said microorganisms that enter said microcosm.

14. A testing device as recited in claim 12 wherein at least one of said microcosms comprises a specified test substance that can diffuse into the fluid flowing through said microcosm.

15. A testing device as recited in claim 12, wherein a test microcosm configured so as to aid in addressing research interests chosen from the group consisting of:
 identification and linking of microbial function occurring in said environment to phylogeny, wherein at least one of said microcosms having placed therein an isotope labeled test compound that can be used in conjunction with stable isotope probing (SIP),
 identification and linking of the microbial function occurring in said environment to phylogeny, wherein at least one of said microcosms having placed therein an isotope labeled test compound that can be used in conjunction with mass spectrometry,
 survival in said environment of a specified microorganism, herein at least one of said microcosms having placed therein said specified microorganism,
 fate in said environment of a specified, genetically engineered microorganism, wherein at least one of said microcosms is configured to contain said genetically engineered microorganism,
 fate in said environment of a specified pathogen, wherein at least one of said microcosms is configured to contain said pathogen,
 for a specified process in said environment, effectiveness of specified, varying test substances for their ability to accelerate said process, wherein said test substances are added to said microcosms,
 identification of microorganisms indigenous to said environment that are responsible for a desired bioremediation process in said environment,
 effectiveness of said varying bioremediation strategies for said environment, wherein said microcosms are configured to be representative of said varying bioremediation strategies,
 effectiveness of said varying bioaugmentation strategies for said environment, wherein said microcosms are configured to be representative of said varying bioaugmentation strategies,
 effectiveness of said varying chemical treatment strategies for said environment, wherein said microcosms are configured to be representative of said varying chemical treatment strategies,
 intrinsic transformation rates in said environment when said environment is contaminated with a specified contaminant
 enhanced transformation rates in said environment when said environment is contaminated with a specified contaminant, wherein specified nutrients are added to said microcosms,
 analysis of a microbial community indigenous to said environment,
 proteomic analysis of a microbial community indigenous to said environment,
 discovery within said environment of novel microorganisms of potential commercial value,
 discovery within said environment of novel biochemical processes of potential commercial value,
 discovery within said environment of a novel natural product of potential commercial value,
 normalization of test results achieved with said device for differences between when and where said tests are conducted, wherein at least one of said microcosms is configured to serve as an internal standard to which said results can be normalized,
 identification of a chemical for enhancing a signal-to-noise ratio in a mass spectrometric analysis of a specified microorganism, wherein at least one of said microcosm configured to foster growth of said microorganism while limiting growth and survival of other, non-specified microorganisms,
 determination of a fate of a specified compound in said environment for a chemical risk assessment, wherein at least one of said microcosms having placed therein said compound,
 determination of an effect of a specified compound on a microbial community of said environment for chemical risk assessment, wherein at least one of said microcosms having placed therein said compound,
 determination of a fate of a specified microorganism for biological risk assessment, wherein at least one of said microcosms having placed therein said microorganism,
 determination of an effect of a specified microorganism on a microbial community of said environment for biological risk assessment, wherein at least one of said microcosms having placed therein said specified microorganism,
 determination, for environmental monitoring purposes of an effect of a specified agent in said environment, wherein at least one of said microcosms having placed therein said agent, said placement being such that said agent is retrievable from said microcosm,
 determination, for risk assessment purposes of an effect of a specified agent in said environment, wherein at least one of said microcosms having placed therein said agent, said placement being such that said agent is retrievable from said microcosm,
 determination, for environmental treatment purposes of an effect of a specified agent in said environment, wherein at least one of said microcosms having placed therein said agent, said placement being such that said agent is retrievable from said microcosm,
 determination, for environmental monitoring purposes of an effect of a specified agent in said environment, wherein at least one of said microcosms having placed therein said agent and said device being configured such that said fluid from the environment that comes into contact with said agent in said microcosm is retrievable, determination, for risk assessment purposes of an effect of a specified agent in said environment, wherein at least one of said microcosms having placed therein said agent and said device being configured such that said fluid from the environment that comes into contact with said agent in said microcosm is retrievable, determination, for environment treatment purposes, of an effect of a specified agent in said environment, wherein at least one of said microcosms having placed therein said agent and said device being configured such that said fluid from the environment that comes into contact with said agent in said microcosm is retrievable, determination, for environmental monitoring purposes of an effect of a specified biochemical process in said environment, wherein said microcosm valve being configured so that the duration of said process in said microcosm is controllable, determination, for risk assessment purposes of the an effect of a specified biochemical process in said environment, wherein said microcosm valve being configured so that the duration of said process in said microcosm is controllable, determination, for environmental treatment purposes, of an effect of a specified biochemical process in said environment, wherein said microcosm valve being configured so that a duration of said process in said microcosm is controllable, elucidation of in situ metabolic activity of a specified microorganism, wherein at least one of said microcosms having placed therein an isotope labeled test compound which is to be analyzed for a ratio of light (non-labeled) and heavy (labeled) biomarkers of said microorganism, and detection of a specified microorganism in said environment, wherein at least one of said microcosms having placed therein a test compound suitable for increasing a signal-to-noise ratio of a characteristic biomarker of a microorganism during mass spectrometric analysis following in situ biomarker amplification.

16. A testing device as recited in claim 12, further comprising a remote control for remotely controlling the operation of said valve for covering said microcosm fluid flow paths.

17. A testing device as recited in claim 1 further comprising at least one of said microcosms configured for fostering the collection of said microorganisms that enter said microcosm.

18. A testing device as recited in claim 1 wherein at least one of said microcosms comprises a specified test substance that can diffuse into the fluid flowing through said microcosm.

19. A testing device as recited in claim 1 wherein said test microcosm is lyophilized and vacuum sealed prior to use.

20. A testing device as recited in claim 19, wherein said microcosm lyophilized and vacuum sealed prior to use contains a test compound, a test substance, a test organelle or a test microorganisms.

21. A testing device as recited in claim 1, wherein a test microcosm configured so as to aid in addressing research interests chosen from the group consisting of:

identification and linking of microbial function occurring in said environment to phylogeny, wherein at least one of said microcosms having placed therein an isotope labeled test compound that can be used in conjunction with stable isotope probing (SIP), identification and linking of the microbial function occurring in said environment to phylogeny, wherein at least one of said microcosms having placed therein an isotope labeled test compound that can be used in conjunction with mass spectrometry, survival in said environment of a specified microorganism, herein at least one of said microcosms having placed therein said specified microorganism, fate in said environment of a specified, genetically engineered microorganism, wherein at least one of said microcosms is configured to contain said genetically engineered microorganism, fate in said environment of a specified pathogen, wherein at least one of said microcosms is configured to contain said pathogen, for a specified process in said environment, effectiveness of specified, varying test substances for their ability to accelerate said process, wherein said test substances are added to said microcosms, identification of microorganisms indigenous to said environment that are responsible for a desired bioremediation process in said environment, effectiveness of varying bioremediation strategies for said environment, wherein said microcosms are configured to be representative of said varying bioremediation strategies, effectiveness of varying bioaugmentation strategies for said environment, wherein said microcosms are configured to be representative of said varying bioaugmentation strategies, effectiveness of varying chemical treatment strategies for said environment, wherein said microcosms are configured to be representative of said varying chemical treatment strategies, intrinsic transformation rates in said environment when said environment is contaminated with a specified contaminant enhanced transformation rates in said environment when said environment is contaminated with a specified contaminant, wherein specified nutrients are added to said microcosms, analysis of a microbial community indigenous to said environment, proteomic analysis of a microbial community indigenous to said environment, discovery within said environment of novel microorganisms of potential commercial value, discovery within said environment of novel biochemical processes of potential commercial value, discovery within said environment of a novel natural product of potential commercial value, normalization of test results achieved with said device for differences between when and where said tests are conducted, wherein at least one of said microcosms is configured to serve as an internal standard to which said results can be normalized, identification of a chemical for enhancing a signal-to-noise ratio in a mass spectrometric analysis of a specified microorganism, wherein at least one of said microcosm configured to foster the growth of said microorganism while limiting the growth and survival of other, non-specified microorganisms, determination of a fate of a specified compound in said environment for a chemical risk assessment, wherein at least one of said microcosms having placed therein said compound, determination of an effect of a specified compound on a microbial community of said environment for chemical risk assessment, wherein at least one of said microcosms having placed therein said compound, determination of a fate of a specified microorganism for biological risk assessment, wherein at least one of said microcosms having placed therein said microorganism, determination of an effect of a specified microorganism on a microbial community of said environment for biological risk assessment, wherein at least one of said microcosms having placed therein said specified microorganism, determination, for environmental monitoring purposes of an effect of a specified agent in said environment, wherein at least one of said microcosms having placed therein said agent, said placement being such that said agent is retrievable from said microcosm, determination, for risk assessment purposes of an effect of a specified agent in said environment, wherein at least one of said microcosms having placed therein said agent, said placement being such that said agent is retrievable from said microcosm, determination, for environmental treatment purposes of an effect of a specified agent in said environment, wherein at least one of said microcosms having placed therein said agent, said placement being such that said agent is retrievable from said microcosm, determination, for environmental monitoring purposes of an effect of a specified agent in said environment, wherein at least one of said microcosms having placed therein said agent and said device being configured such that said fluid from the environment that comes into contact with said agent in said microcosm is retrievable, determination, for risk assessment purposes of an effect of a specified agent in said environment, wherein at least one of said microcosms having placed therein said agent and said device being configured such that said fluid from the environment that comes into contact with said agent in said microcosm is retrievable, determination, for environment treatment purposes, of an effect of a specified agent in said environment, wherein at least one of said microcosms having placed therein said agent and said device being configured such that said fluid from the environment that comes into contact with said agent in said microcosm is retrievable, determination, for environmental monitoring purposes, of an effect of a specified biochemical process in said environment, wherein said microcosm valve being configured so that the duration of said process in said microcosm is controllable, determination, for risk assessment purposes, of an effect of a specified biochemical process in said environment, wherein said microcosm valve being configured so that the duration of said process in said microcosm is controllable, determination, for environmental treatment purposes, of an effect of a specified biochemical process in said environment, wherein said microcosm valve being configured so that a duration of said process in said microcosm is controllable, elucidation of in situ metabolic activity of a specified microorganism, wherein at least one of said microcosms having placed therein an isotope labeled test compound which is to be analyzed for a ratio of light (non-labeled) and heavy (labeled) biomarkers of said microorganism, and detection of a specified microorganism in said environment, wherein at least one of said microcosms having placed therein a test compound suitable for increasing a signal-to-noise ratio of a characteristic biomarker of a microorganism during mass spectrometric analysis following in situ biomarker amplification.

22. A testing device as recited in claim 1, further comprising a remote control for remotely controlling the operation of said valve for covering said microcosm fluid flow paths.

* * * * *